(12) United States Patent
Voll Barclay et al.

(10) Patent No.: US 6,642,402 B2
(45) Date of Patent: Nov. 4, 2003

(54) SYNTHESIS OF BIS (CYCLOPENTADIENYL) AND BIS (INDENYL) RUTHENIUM COMPLEXES

(75) Inventors: Karin A. Voll Barclay, Boulder, CO (US); Jeffrey M. Sullivan, Loveland, CO (US); Dawn A. Arkin, Longmont, CO (US); Fredric R. Askham, Loveland, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 10/178,014

(22) Filed: Jun. 21, 2002

(65) Prior Publication Data

US 2003/0045737 A1 Mar. 6, 2003

Related U.S. Application Data

(63) Continuation-in-part of application No. 09/938,952, filed on Aug. 24, 2001, now abandoned, which is a continuation-in-part of application No. 09/845,627, filed on Apr. 30, 2001, now abandoned.

(51) Int. Cl.$^7$ .......................... C07F 17/02; C23C 16/18
(52) U.S. Cl. ........................................ 556/136; 427/252
(58) Field of Search ............................ 556/136; 427/252

(56) References Cited

U.S. PATENT DOCUMENTS

| | | | | |
|---|---|---|---|---|
| 6,002,036 A | * | 12/1999 | Kadokura | 556/136 |
| 6,521,772 B1 | * | 2/2003 | Lienhard et al. | 556/136 |
| 2002/0058106 A1 | * | 5/2002 | Okamoto et al. | 427/250 |
| 2002/0064948 A1 | * | 5/2002 | Saito et al. | 438/681 |
| 2002/0065427 A1 | * | 5/2002 | Okamoto | 556/136 |
| 2002/0103395 A1 | * | 8/2002 | Saito | 556/136 |

* cited by examiner

*Primary Examiner*—Porfirio Nazario-Gonzalez
(74) *Attorney, Agent, or Firm*—Edward S. Irons

(57) ABSTRACT

A process for preparing a cyclopentadienyl or indenyl ruthenium complex by treatment of a cyclopentadienyl or indenyl compound with ruthenium trichloride dihydrate and magnesium powder in an alkanol at 10° C. to −30° C. is described.

11 Claims, No Drawings

SYNTHESIS OF BIS (CYCLOPENTADIENYL) AND BIS (INDENYL) RUTHENIUM COMPLEXES

This application is a continuation-in-part of U.S. patent application Ser. No. 09/938,952 filed Aug. 24, 2001 now abandoned, which in turn is a continuation-in-part of U.S. patent application Ser. No. 09/845,627 filed Apr. 30, 2001 now abandoned.

FIELD OF THE INVENTION

This invention relates to bis(cyclopentadienyl) and bis (indenyl) ruthenium complexes which are useful in chemical vapor deposition (CV) and other procedures.

BACKGROUND OF THE INVENTION

The state of the art relevant to this invention as of Jul. 17, 1997 is summarized in U.S. Pat. No. 6,002,036. A process for the synthesis of bis(alkylcyclopentadienyl) ruthenium complexes by treatment of $RuCl_3$ hydrates and ethylcyclopentadiene or isopropylcyclopentadiene with zinc powder in an alcohol solvent at $-30°$ C. to $0°$ C. is described.

SUMMARY OF THE INVENTION

The invention comprises synthesis of bis (cyclopentadienyl), bis(alkylcyclopentadienyl), bis(indenyl) or bis(alkylindenyl) liquid and solid ruthenium complexes by treating ruthenium trichloride hydrate and a cyclopentadienyl compound or an indenyl compound with magnesium powder in $C_2$ to $C_8$ alkanol, e.g., ethanol. The treating may be accomplished at a temperature from about $10°$ C. to about $-30°$ C.

DEFINITIONS

As used in this specification, the following terms have the meaning set forth:
(1) Cyclopentadienyl Compound
A compound of the formula

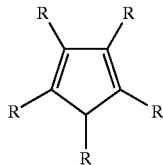

in which each R is independently hydrogen or a $C_1$ to $C_{10}$ alkyl group. $C_1$ to $C_5$ monoalkyl cyclopentadienyl compounds are preferred.
(2) Indenyl Compound
A compound of formula

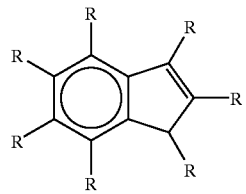

in which each R is independently hydrogen or a $C_1$ to $C_{10}$ alkyl group. $C_1$ to $C_5$ monoindenyl compounds are preferred.

DETAILED DESCRIPTION OF THE INVENTION

Ruthenium trichloride dihydrate, a cyclopentadienyl or indenyl compound, and an alkanol, preferably ethanol, are combined and treated with magnesium powder of about minus 100 (−100) to 200 mesh at low temperatures with an appropriate stir out. A bis(cyclopentadienyl) or bis(indenyl) ruthenocene may be isolated by filtration, followed by combination with an aliphatic or aromatic hydrocarbon solvent, preferably hexane or toluene, another filtration, and subsequent passage through a silica column. Final products, if solids, may be isolated in >99% purity in yields of about 65 weight percent by crystallization from a hydrocarbon solvent. High purity liquid products may be isolated by fractional distillation.

EXAMPLE 1

Ethyl Ruthenocene-Yellow Oil Product

Ruthenium trichloride dihydrate is dissolved in ethanol. The solution is cooled to $-20$ C. to $-30°$ C. and 4.0 to 4.4 equivalents of ethylcyclopentadiene (EtCp) are added. Over the course of 1 hr to 1.5 hr, magnesium powder (minus 100 mesh) (3.0 equivalents) is added as the pot temperature is maintained at $-10°$ C. to $-30°$ C. The consequent reaction mixture is stirred out for about 19 hours at $10–15°$ C., or until gas chromatography analysis indicates that the reaction is complete. Thereafter, the reaction mixture is filtered, and the ethanol and unreacted ethyl cyclopentadiene are removed under vacuum. Nexane and 3.0 equivalents of $Na_2SO_4$ are added to the remaining slurry which is then stirred for 1–20 hrs. The solids are removed by filtration through Celite. The remaining yellow solution is distilled under vacuum to an oil. The yellow oil can be isolated in >99% purity with yields of 65%. Hexane is added back to the oil, followed by a filtration through Celite® or silica. A final run through a silica column may be appropriate to remove any color bodies.

Hexane is stripped from the yellow solution so produced. Pentane is added to the residual oil, and the product, $(EtCp)_2Ru$, is crystallized at $-30°$ C. After removal of the supernatant, the pentane is then pumped off under vacuum. More than one crystallization may be appropriate to enhance purity. This synthesis is illustrated by equation 1:

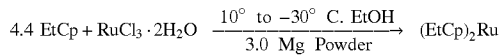

| 94 g/mol | 243.5 g/mol | 24.3 g/mol | 288 g/mol |
| 4.576 mol | 1.04 mol | 3.12 mol | 1.04 mol |
| 430 g | 253.2 g | 75.8 g | 300 g |

Equation 1

Any cyclopentadienyl or any indenyl compound as defined herein may be substituted for ethylcyclopentadiene in Example 1.

Magnesium powder of any desired mesh size, preferably minus 100 (−100) to 200 mesh, may be used. Any $C_2$ to $C_8$ alkanol may be used instead of ethanol.

Alternatively, a preformed alkanol solution of ruthenium trichloride dihydrate may be added to a preformed slurry of magnesium powder and alkyl cyclopentadiene at a temperature of about $0°$ C. to

EXAMPLE 2

Unsubstituted Ruthenocene-Crystalline Product

A magnesium slurry was produced by adding 45.62 g of minus 100 (−100) mesh magnesium powder (made by READE) (1.88 moles, 3 equivalents) slowly to a 5 liter vessel containing 1.2L of ethanol (Filmex) at room temperature (25° C.). 323.00 g of 76.8% pure cyclopentadiene (3.75 moles) at a temperature of about −50° C. was added to the magnesium slurry, which was at room temperature, through an addition funnel. To this, a 0.35M solution of $RuCl_3*1.8H_2O$ in ethanol (Filmex) (0.625 moles in 1.8L of ethanol) was added over a 2.5 hour time period, via addition funnel, between −10° C. and 10° C. The slurry turned sequentially from a grey color to brown to green to blue, and then back to grey/brown as each addition of ruthenium trichloride was made. The mixture was then stirred at a temperature of from 5° C. to 10° C. for 3 hours, and was then stirred out to room temperature overnight. The ethanol was then distilled off under rough pump, and about three to four liters of toluene was added back. The distillation was switched from rough pump to atmospheric pressure and was continued until a pot temperature of 110° C. was reached. The yellow solution was hot filtered (100° C.) through a cake of Celite® that had been washed with hot toluene (100° C.). The filtrate was concentrated by distillation until the yellow solution reached a volume of 650 mL. The yellow product crystallized out of the toluene solution as it cooled to room temperature. The yellow slurry was further cooled in a dry ice/acetone bath, and the light yellow crystalline solids were filtered on to a Buchner funnel, washed with 100 mL of hexane, and pumped dry giving 134.3 g of ruthenocene (93% yield from first crop).

We claim:

1. A process for producing a cyclopentadienyl or an indenyl ruthenocene complex which comprises treating a cyclopentadienyl or an indenyl compound with ruthenium trichloride hydrate and magnesium powder.

2. The process of claim 1 wherein said treating of said cyclopentadienyl compound or said indenyl compound is accomplished in the presence of a $C_2$ to $C_8$ alkanol.

3. The process of claim 1 or claim 2 wherein said treating takes place at a temperature of 10° C. to −30° C.

4. The process of claim 2 wherein said alkanol solvent is ethanol.

5. The process of claim 1 wherein the mesh size of said magnesium powder is from about 50 mesh to about 200 mesh.

6. The process of claim 1 wherein the mesh size of said magnesium powder is from about minus 100 mesh to about 200 mesh.

7. The process which comprises:

(i) treating a $C_2$ to $C_5$ monoalkyl cyclopentadiene with ruthenium trichloride hydrate and magnesium powder, wherein said treating is accomplished in the presence of ethanol and
wherein said treating takes place at a temperature of 10° C. to −30° C. to produce a reaction mixture;

(ii) agitating said step (i) reaction mixture at about 10° C. to about 15° C. for a time period appropriate to complete the reaction
wherein an ethanol solution of $C_2$ to $C_5$ ruthenocene is produced in situ in said reaction mixture; and (iii) isolating said $C_2$ to $C_5$ ruthenocene from said step (ii) ethanol solution.

8. The process of claim 7 wherein said $C_2$ to $C_5$ monoalkyl cyclopentadiene of step (i) is ethyl cyclopentadiene and wherein said $C_2$ to $C_5$ ruthenocene of steps (ii) and (iii) is ethyl ruthenocene.

9. A process for producing ruthenocene which comprises treating cyclopentadiene with ruthenium trichloride hydrate in the presence of magnesium powder.

10. A method for producing ethyl ruthenocene which comprises:

(i) providing an ethanol solution of ruthenium trichloride hydrate;

(ii) providing a slurry of magnesium powder and ethyl cyclopentadiene in ethanol; and (iii) adding said step (i) solution to said step (ii) slurry at a temperature of from about 10° C. to about −10° C. wherein a reaction mixture containing an ethanol solution of ethyl ruthenocene is produced.

11. The method of claim 10 further comprising a step (iv) isolating said ethyl ruthenocene from said step (iii) reaction mixture.

* * * * *